(12) United States Patent
Leflaive et al.

(10) Patent No.: US 9,731,220 B2
(45) Date of Patent: *Aug. 15, 2017

(54) PROCESS AND APPARATUS FOR SIMULATED COUNTER-CURRENT CHROMATOGRAPHIC SEPARATION USING TWO ADSORBERS IN PARALLEL FOR OPTIMIZED PARA-XYLENE PRODUCTION

(75) Inventors: Philibert Leflaive, Mions (FR); Damien Leinekugel Le Cocq, Lyons (FR); Gerard Hotier, Rueil Malmaison (FR); Luc Wolff, Chaponnay (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 1464 days.

This patent is subject to a terminal disclaimer.

(21) Appl. No.: 13/495,423

(22) Filed: Jun. 13, 2012

(65) Prior Publication Data

US 2013/0006031 A1 Jan. 3, 2013

(30) Foreign Application Priority Data

Jun. 16, 2011 (FR) ..................... 11 01855

(51) Int. Cl.
*C07C 7/13* (2006.01)
*B01D 15/18* (2006.01)
(52) U.S. Cl.
CPC ........... *B01D 15/1821* (2013.01); *C07C 7/13* (2013.01)
(58) Field of Classification Search
None
See application file for complete search history.

(56) References Cited

U.S. PATENT DOCUMENTS

| | | | |
|---|---|---|---|
| 4,434,051 A * | 2/1984 | Golem | B01D 15/1842 210/264 |
| 5,470,482 A | 11/1995 | Holt | |
| 7,208,651 B2 | 4/2007 | Frey | |
| 8,013,202 B2 | 9/2011 | Lee et al. | |
| 8,030,533 B2 | 10/2011 | Hotier et al. | |
| 2006/0199989 A1 | 9/2006 | Frey | |
| 2009/0069612 A1 | 3/2009 | Hotier et al. | |
| 2009/0234170 A1 | 9/2009 | Lee et al. | |

FOREIGN PATENT DOCUMENTS

| FR | 2 883 283 A1 | 9/2006 |
|---|---|---|
| WO | 2006/096394 A2 | 9/2006 |

OTHER PUBLICATIONS

Lim, Y., et al., "Improvement of para-Xylene SMB Process Performance on an Industrial Scale," Industrial & Engineering Chemistry Research, Apr. 2010, vol. 49, No. 7, pp. 3316-3327; Cited in Search Report, dated Jan. 13, 2012, issued in FR 11/01.855.

Search Report and Written Opinion, dated Jan. 13, 2012, issued in FR 11/01.855.

* cited by examiner

*Primary Examiner* — Tam M Nguyen
(74) *Attorney, Agent, or Firm* — Millen, White, Zelano and Branigan, P.C.

(57) ABSTRACT

The present invention describes a novel configuration for simulated moving bed separation processes characterized by using two adsorbers each containing 12 beds, these two adsorbers functioning in parallel. This novel configuration can be used to optimize para-xylene production.

11 Claims, 2 Drawing Sheets

PROCESS AND APPARATUS FOR SIMULATED COUNTER-CURRENT CHROMATOGRAPHIC SEPARATION USING TWO ADSORBERS IN PARALLEL FOR OPTIMIZED PARA-XYLENE PRODUCTION

FIELD OF THE INVENTION

The invention relates to the field of separating para-xylene from other aromatic C8 isomers. To carry out such separation, a family of processes and associated devices is used, which is known under the name of simulated moving bed separation processes or simulated counter-current separation, or as the VARICOL process; we shall hereinafter use the general term of SCC separation processes.

PRIOR ART

SCC separation is well known in the art. As a general rule, a para-xylene separation process functioning in simulated counter-current mode comprises at least four zones, and possibly five or six, each of those zones being constituted by a certain number of successive beds, and each zone being defined by its position included between a supply point and a withdrawal point. Typically, a SCC unit for the production of para-xylene is supplied by at least one feed F to be fractionated (containing para-xylene and the other aromatic C8 isomers) and a desorbant D, occasionally termed the eluent (generally para-diethylbenzene or toluene), and from said unit at least one raffinate R containing the isomers of para-xylene and desorbant and an extract E containing para-xylene and desorbant are withdrawn.

Other injection-withdrawal points may be added in order to rinse the distribution circuits, as described, for example, in patent U.S. Pat. No. 7,208,651. Adding such supplemental rinsing streams does not in any way change the principle of the function of the SCC; for the sake of brevity, we shall not add these supplemental injection and withdrawal points to the description of the process of the invention.

The supply and withdrawal points are modified over time, shifted in the same direction by a value corresponding to one bed. The various injection or withdrawal points may be shifted either simultaneously or non-simultaneously, as disclosed in patent U.S. Pat. No. 6,136,198. The process in accordance with this second functional mode is known as the VARICOL process.

Conventionally, four different chromatographic zones are defined in a SCC unit:
  zone 1: para-xylene desorption zone, included between the injection of desorbant D and the removal of extract E;
  zone 2: isomers of para-xylene desorption zone, included between the removal of the extract E and the injection of the feed to be fractionated F;
  zone 3: para-xylene adsorption zone, included between the injection of the feed and the withdrawal of the raffinate R;
  zone 4: zone located between the withdrawal of the raffinate R and the injection of the desorbant D.

As described by Lim et al (2010, Ind Eng Chem Res, vol 49, p 3316-3327), the process for the separation of para-xylene by SCC is generally composed of 24 beds, distributed among 2 adsorbers each containing 12 beds. The 2 adsorbers are connected in series, and the SCC cycle thus comprises 24 steps during which each stream (D, E, F, R) is injected or withdrawn downstream of each of the 24 beds.

The term "connection in series" for the two adsorbers of twelve beds means the following 3 features:
  the twelfth bed of the first adsorber is connected to the first bed of the second adsorber via a line containing at least one recirculation pump and possibly other equipment such as a flow meter, a pressure sensor, etc.;
  the twelfth bed of the second adsorber is connected to the first bed of the first adsorber via a line containing at least one recirculation pump and possibly other equipment such as a flow meter, a pressure sensor, etc.;
  the assembly of the two adsorbers has 1 point for introducing feed, 1 point for introducing eluent, 1 point for withdrawing raffinate and 1 point for withdrawing extract.

It is important that these characteristics are borne in mind as they are modified in the parallel configuration of the invention, as will be developed below.

The pressure drops occurring in a SCC process are directly linked to the interstitial velocities of the fluid phase in the beds of adsorbent.

The term "interstitial velocity" means the actual velocity of fluid between the particles constituting the solid adsorbent. The pressure drops play an important role in sizing the recirculation pump or pumps, the thickness of the adsorber walls, the size of the support systems for the distributor plates, the mechanical behaviour of the grains of adsorbent, etc.

The interstitial velocity may also play a very important role as regards the mechanical behaviour of the grains of adsorbent and may even become a limiting factor in operating a SCC unit.

It is known from the prior art (in particular from patents U.S. Pat. No. 7,649,124 and U.S. Pat. No. 7,635,795) that the process for the production of para-xylene by SCC has a limited productivity. Solutions have been proposed in the prior art to improve this process:
  patents FR 2 743 068 and U.S. Pat. No. 7,635,795 present processes using several adsorption steps. The first step is intended to produce a stream enriched in para-xylene with a purity insufficient to allow it to be used commercially (<99% by weight). The second step can be used to obtain very high purity para-xylene. In particular, FIG. 5 of U.S. Pat. No. 7,635,795 illustrates the debottlenecking of a pre-existing unit by 24-bed SCC by adding an adsorber for pre-treatment of the feed;
  patents FR 2 693 186, FR 2 757 507 and U.S. Pat. No. 7,649,124 present processes using a step for SCC adsorption in combination with crystallization. The first step is intended to produce, by SCC, a stream enriched in para-xylene with a purity which is insufficient to allow it to be used commercially (typically of the order of 90% by weight). The second step can be used to obtain very high purity para-xylene by crystallization. In particular, FIG. 5 of U.S. Pat. No. 7,649,124 illustrates the debottlenecking of a pre-existing unit by 24-bed SCC (composed of two 12-bed adsorbers) by means of a modification to an adsorption process using two adsorbers in parallel and adding a crystallization step to post-treat the extracts.

All of the solutions recommended in the prior art to solve the problem of limiting the production of units for the production of para-xylene using a 24-bed simulated moving bed thus consists of adding a separation stage either using an adsorber to pre-treat the feed and/or a post-treatment of the extract(s) by crystallization, giving rise to very substantial costs.

The aim of the process of the invention is to solve the problem of the limitation to productivity of 24-bed para-xylene production units without the disadvantage of the prior art solutions using two adsorbers in parallel, each adsorber comprising 12 beds, in order to produce high purity para-xylene (i.e. more than 99.7% pure) directly.

It has surprisingly been shown that by using two 12-bed adsorbers and suitable operating conditions (configuration, switch period, flow rates, water content of adsorbent, temperature and quantity of solvent) in a configuration known as "parallel", a quantity of para-xylene of commercial purity (i.e. more than 99.7% by weight pure) can be produced which is higher than the quantity produced by a unit using two adsorbers in a conventional manner with a 24-bed in series configuration.

It has also been observed that the modifications to be provided to a pre-existing 24-bed unit in order to obtain the process or unit of the invention are relatively slight and do not require major investment.

Thus, the present invention is particularly suitable for the case in which revamping of a 24-bed unit into two 12-bed units is to be carried out.

BRIEF DESCRIPTION OF THE FIGURES

In the prior art, there is one feed injection point (F), one desorbant introduction point (D), one extract withdrawal point (E) and one raffinate withdrawal point (R).

For each adsorber, there is injection of a stream of feed (Fa for adsorber a, and Fb for adsorber b), of a stream of desorbant (Da for adsorber a, and Db for adsorber b), withdrawing a stream of extract (Ea for adsorber a and Eb for adsorber b) and of a stream of raffinate (Ra for adsorber a and Rb for adsorber b).

The recirculation pump for adsorber a is denoted Pa and the recirculation pump for adsorber b is denoted Pb. The single replacement pump for the recirculation pumps is denoted Pc. The set of valves (Vc1 to Vc4) and the dashed lines (corresponding to lines which are not used when the replacement pump Pc is not in use) means that the pump Pc can be used either in place of pump Pa of adsorber a or in place of pump Pb of adsorber b.

BRIEF DESCRIPTION OF THE INVENTION

The present invention can be defined as a process for the simulated counter-current separation of xylenes using two adsorbers each comprising twelve beds, these two adsorbers functioning in an "in parallel" configuration.

More precisely, the process for simulated counter-current separation of xylenes of the present invention comprises a first adsorption step using two adsorbers each containing twelve beds, each of the adsorbers having a line for introducing feed (F), a line for introducing eluent (D), a line for withdrawing extract (E) and a line for withdrawing raffinate (R) and is divided into 4 chromatographic zones defined as follows:

zone 1: para-xylene desorption zone, included between the injection of desorbant D and the removal of extract E;

zone 2: isomers of para-xylene desorption zone, included between the removal of the extract E and the injection of the feed to be fractionated F;

zone 3: para-xylene adsorption zone, included between the injection of the feed and the withdrawal of the raffinate R;

zone 4: zone located between the withdrawal of the raffinate R and the injection of the desorbant;

and the two adsorbers function in parallel, i.e. the twelfth bed of the first adsorber (a) is connected to the first bed of said adsorber (a) via a line containing a recirculation pump (Pa) and the twelfth bed of the second adsorber (b) is connected to the first bed of said second adsorber (b) via a line containing a recirculation pump (Pb) which is distinct from the preceding pump, the process further comprising:

a step for distilling a mixture of the two raffinates in a single distillation column from which a mixture of xylenes depleted in para-xylene is withdrawn overhead and the desorbant, which is recycled, is withdrawn from the bottom;

a step for distilling the two extracts in one or two distillation column(s) from which substantially pure para-xylene (i.e. with a purity of more than 99.7% by weight) is withdrawn overhead and the desorbant is withdrawn from the bottom and recycled.

As in all simulated moving bed processes, the feed and desorbant injection points and the extract and raffinate withdrawal points are shifted by one bed at each time increment. The term "cycle" is used for the time necessary for the injection and withdrawal points to return to their initial position. This notion is particularly important in the variation known as "VARICOL" which can be used to define the non-integral numbers of beds per zone using the mean value for these numbers of beds per zone during a cycle.

In a first variation (1) of the process of the invention, the distribution of the beds in each adsorber is fixed as a function of the various chromatographic zones. This distribution does not vary during a cycle.

The 12 beds of each adsorber are distributed in the 4 chromatographic zones in the following manner:
2 beds in zone 1;
5 beds in zone 2;
3 beds in zone 3;
2 beds in zone 4.

In a second variation (2) of the process of the invention, one of the adsorbers functions in fixed mode and the second adsorber functions in "Varicol" mode.

For the adsorber functioning in fixed mode, the 12 beds of the adsorber are distributed in the 4 chromatographic zones in the following manner:
2 beds in zone 1;
5 beds in zone 2;
3 beds in zone 3;
2 beds in zone 4;
and for the other adsorber functioning in "Varicol" mode, the shifts of the 2 injection points and the 2 withdrawal points are not simultaneous, in order to obtain mean numbers of beds per zone which are not whole numbers during a cycle.

The numbers of beds per zone for this adsorber are as follows:
2.5 (+or −0.5) beds in zone 1;
4.5 (+or −0.5) beds in zone 2;
3.5 (+or −0.5) beds in zone 3;
1.5 (+or −0.5) beds in zone 4.

In a third variation (3) of the process of the invention, each of the two adsorbers functions in "Varicol" mode. The shifts of the 2 injection points and the 2 withdrawal points for each of the two adsorbers are not simultaneous, in order to obtain mean numbers of beds per zone which are not whole numbers during a cycle.

The numbers of beds per zone for this adsorber are as follows:
- 2.5 (+or −0.5) beds in zone 1;
- 4.5 (+or −0.5) beds in zone 2;
- 3.5 (+or −0.5) beds in zone 3;
- 1.5 (+or −0.5) beds in zone 4.

In another variation of the process which is compatible with the three variations (1), (2), (3) discussed above, the two adsorbers each contain twelve beds separated by plates Pi with a chamber for distribution and/or extraction of fluids and programmed means for sequential distribution and extraction of said fluids.

These programmed means for distribution and extraction of fluids are constituted, for each plate Pi, by at least 4 programmed 2-way on-off valves to respectively manage the 2 fluid supplies for feed (F) and eluent (D) and the 2 withdrawals, for extract (E) and raffinate (R).

In accordance with another variation of the process for simulated counter-current separation of xylenes of the invention, each adsorber uses a rotary multi-way valve which can manage the supply of the feed (F), the supply of the eluent (D), the withdrawal of the extract (E) and the withdrawal of the raffinate (R) for all of the plates.

The process for simulated counter-current separation of xylenes of the invention generally makes use of an agglomerated zeolitic adsorbent solid comprising small crystals, i.e. with a diameter of 2 microns (μm) or less, of X zeolite at least 90% exchanged either by barium ions alone or by barium ions and potassium ions, the exchangeable sites occupied by potassium representing up to ⅓ of the exchangeable sites occupied by barium+potassium ions, and a proportion of inert binder of less than 15% by weight.

Preferably, the process for simulated counter-current separation of xylenes of the invention makes use of a desorbant which is para-diethylbenzene.

The operating conditions of the process for simulated counter-current separation of xylenes of the invention are generally in the following ranges:
- the adsorption temperature is in the range 100° C. to 250° C., preferably in the range 120° C. to 180° C.;
- the adsorption pressure is in the range between the bubble-point pressure of xylenes at the temperature of the process and $30 \times 10^5$ Pa;
- the ratio of the flow rates of desorbant to feed is in the range 0.7 to 2.5;
- the recycle ratio of the eluent is in the range 2.5 to 12, preferably in the range 3.5 to 6;
- the duration of the cycle followed by the adsorbers is in the range 14 to 30 minutes, preferably in the range 18 to 23 minutes;
- the mean linear velocity with respect to the empty reactor is in the range 0.7 cm/s to 1.4 cm/s, preferably in the range 0.85 cm/s to 1.1 cm/s;
- the water content in the liquid phase is maintained at a content in the range 70 to 140 ppm (by weight), preferably in the range 80 to 120 ppm (by weight).

The process for simulated counter-current separation of xylenes of the invention thus comprises two adsorbers each of 12 beds functioning in parallel and further comprises:
- a single pump replacing the pump(s) for supplying feed (F) and a single pump replacing the pump(s) supplying desorbant (D);
- a single replacement recirculation pump (Pc), said single replacement pump being able to be used either to replace the recirculation pump (Pa) employed on the first adsorber (a), or to replace the recirculation pump (Pb) employed on the second adsorber (b).

DETAILED DESCRIPTION OF THE INVENTION

The present invention concerns a process for the separation of para-xylene from a feed F essentially comprising para-xylene and its aromatic C8 isomers, comprising:
- an adsorption step by simulated counter-current chromatography (SCC) using two adsorbers each with twelve beds, characterized in that the two adsorbers function in parallel, i.e. with a feed introduction point, an eluent introduction point, an extract withdrawal point and a raffinate withdrawal point for each of the adsorbers so as to produce two extracts (one for each adsorber) containing a mixture of xylenes enriched in para-xylene mixed with desorbant, and two raffinates (one for each adsorber) containing a mixture of xylenes depleted in para-xylene with desorbant.
  The term "two adsorbers functioning in parallel" means that the twelfth bed of the first adsorber is connected to the first bed of said first adsorber and the fact that, in the same manner, the twelfth bed of the second adsorber is connected to the first bed of said second adsorber;
- a step for distilling a mixture of the two raffinates in a single distillation column from which a mixture of xylenes depleted in para-xylene is withdrawn overhead and the desorbant which may be recycled is withdrawn from the bottom;
- a step for distilling the two extracts in one or two distillation column(s) from which substantially pure para-xylene is withdrawn overhead (i.e. with a purity of more than 99.7% by weight) and a desorbant is withdrawn from the bottom which may be recycled. Preferably, a single distillation column is used to treat the mixture of the two extracts.

The adsorption step by simulated counter-current chromatography (SCC) of the process of the invention has three variations concerning the distribution of the beds of adsorbent in the various chromatographic zones of each of the adsorbers.

The 4 chromatographic zones are in general defined as follows:
- zone 1: para-xylene desorption zone, included between the injection of desorbant D and the removal of extract E;
- zone 2: isomers of para-xylene desorption zone, included between the removal of the extract E and the injection of the feed to be fractionated F;
- zone 3: para-xylene adsorption zone, included between the injection of the feed and the withdrawal of the raffinate R;
- zone 4: zone located between the withdrawal of the raffinate R and the injection of the desorbant D.

in the first variation a) of the process of the invention, the shifts for the various injection and withdrawal points are simultaneous, the beds of each of the two adsorbers are distributed in the various zones as follows:
- 2 beds in zone 1;
- 5 beds in zone 2;
- 3 beds in zone 3;
- 2 beds in zone 4.

In accordance with the second variation b) of the process of the invention, for one of the adsorbers the shifts of the 2 injection points and the 2 withdrawal points are simultaneous, the 12 beds of the adsorber being distributed in the 4 chromatographic zones in the following manner:

2 beds in zone 1;
5 beds in zone 2;
3 beds in zone 3;
2 beds in zone 4;

and for the other adsorber, the shifts of the 2 injection points and the 2 withdrawal points are not simultaneous, in order to obtain mean numbers of beds per zone which are not whole numbers during a cycle, the numbers of beds per zone for this adsorber being as follows:

2.5 (+or −0.5) beds in zone 1;
4.5 (+or −0.5) beds in zone 2;
3.5 (+or −0.5) beds in zone 3;
1.5 (+or −0.5) beds in zone 4.

In accordance with the third variation c) of the process of the invention, for each of the adsorbers, the shifts of the 2 injection points and the 2 withdrawal points are not simultaneous, in order to obtain mean numbers of beds per zone which are not whole numbers during a cycle, the numbers of beds per zone for each adsorber being as follows:

2.5 (+or −0.5) beds in zone 1;
4.5 (+or −0.5) beds in zone 2;
3.5 (+or −0.5) beds in zone 3;
1.5 (+or −0.5) beds in zone 4.

The adsorbers each contain twelve beds separated by plates Pi with a chamber for distribution and/or extraction of fluids in or from the various beds of adsorbent, and programmed means for sequential distribution and extraction of fluids.

Said programmed means for sequential distribution and extraction of fluids are typically one of the following two major types of technology:

either for each plate, a plurality of programmed on-off valves for supply or withdrawal of fluids, these valves typically being located in the immediate vicinity of the corresponding plate, and for each plate Pi comprising at least 4 programmed 2-way on-off valves respectively for the 2 supplies of fluids F and D and the 2 withdrawals of fluids E and R;

or a rotary multi-way valve for supply or withdrawal of fluids over all of the plates.

The adsorption step of the process of the invention has devices for rinsing the injection and withdrawal networks necessary in order to obtain a para-xylene purity of 99.7% by weight or more. Two cases can be distinguished regarding the network rinsing devices which might be employed in the process of the invention:

the first device consists of flushing the injection/withdrawal network of a given plate with desorbant or relatively pure para-xylene. To this end, for example, a stream is withdrawn from zone 1 (so that the network associated with zone 1 can be flushed) and said stream is re-injected into zone 2 (so that the network associated with zone 2 can be flushed). It is also possible to inject a small stream of extract or para-xylene after distillation into the plate of zone 2 closest to the extract withdrawal point. Other possibilities for rinsing by injection and withdrawal are possible. Such devices have been described, in particular in patents U.S. Pat. Nos. 3,201,491, 5,750,820, 5,912,395, 6,149,874 and WO 2006/096394. Preferably, this rinsing device will be employed when the supply or withdrawal of fluids over all of the plates is carried out using a rotary multi-way valve;

the second device consists of passing a majority of the principal stream into the interior of the adsorber and a minority of that stream (typically 1% to 20% of the principal stream) outside via external bypass lines between successive plates. This flushing of the injection/withdrawal network at a plate by a stream originating from the upper plate is typically carried out continuously such that the lines and zones of the injection/withdrawal network are no longer "dead" but are constantly flushed. Such devices have in particular been described in patents FR 2 935 100, FR 2 935 101 and FR 2 944 215. Preferably, this rinsing device will be employed when supply or withdrawing the fluids over all of the plates is carried out via a plurality of programmed on-off valves.

In accordance with one characteristic of the process, the adsorbent used in the adsorption step may comprise a faujasite type zeolite exchanged with barium or exchanged with barium and potassium.

Preferably, the adsorbent is an agglomerated zeolitic adsorbent solid comprising small crystals (i.e. with a diameter of 2 µm or less) of X zeolite at least 90% exchanged either by barium ions alone or by barium ions and potassium ions, the exchangeable sites occupied by potassium representing up to ⅓ of the exchangeable sites occupied by barium+potassium ions (any complement generally being provided by alkali or alkaline-earth ions other than barium and potassium). The small crystals also comprise a small proportion of inert binder, i.e. less than 15% by weight.

The loss on ignition measured at 900° C. is in the range 4.0% to 7.7% by weight, preferably in the range 4.7% to 6.7% by weight. More preferably, the adsorbent has a very low proportion of inert binder, i.e. less than 5% by weight; the adsorbent is termed "binderless".

The preferred desorbant is para-diethylbenzene, however other desorbants such as toluene, para-difluorobenzene or diethylbenzenes as a mixture may also be suitable. Preferably, para-diethylbenzene is recommended because it is easy to recover by distillation and has a high affinity for the adsorbent.

In accordance with another characteristic of the process, the operating conditions for the adsorption step are as follows:

the temperature is 100° C. to 250° C., preferably 120° C. to 180° C.;

the pressure is between the bubble-point pressure of xylenes at the temperature of the process and $30 \times 10^5$ Pa;

the ratio of the flow rates of desorbant to feed is 0.7 to 2.5;

the recycle ratio is in the range 2.5 to 12, preferably 3.5 to 6; the recycle ratio is defined as the ratio between the mean flow rate flowing in the various beds of adsorbent and the flow rate of feed injected into this adsorber;

the duration of the cycle followed by the adsorbers is in the range 14 to 30 minutes, preferably in the range 18 to 23 minutes;

the mean linear velocity with respect to the empty reactor is in the range 0.7 cm/s to 1.4 cm/s, preferably in the range 0.85 cm/s to 1.1 cm/s;

the water content in the liquid phase is maintained at a content in the range 70 to 140 ppm (by weight), preferably in the range 80 to 120 ppm (by weight).

The process of the present invention can be used to obtain a para-xylene yield of more than 90%, preferably more than 95%, and more preferably more than 98%.

The productivity reached by the process of the invention is in the range 60 kg to 180 kg of para-xylene produced per hour per m³ of adsorbent bed, preferably in the range 75 kg to 140 kg of para-xylene produced per hour per m³ of adsorbent bed, still more preferably in the range 90 kg to 130 kg of para-xylene produced per hour per m³ of bed of adsorbent.

Figure 2:
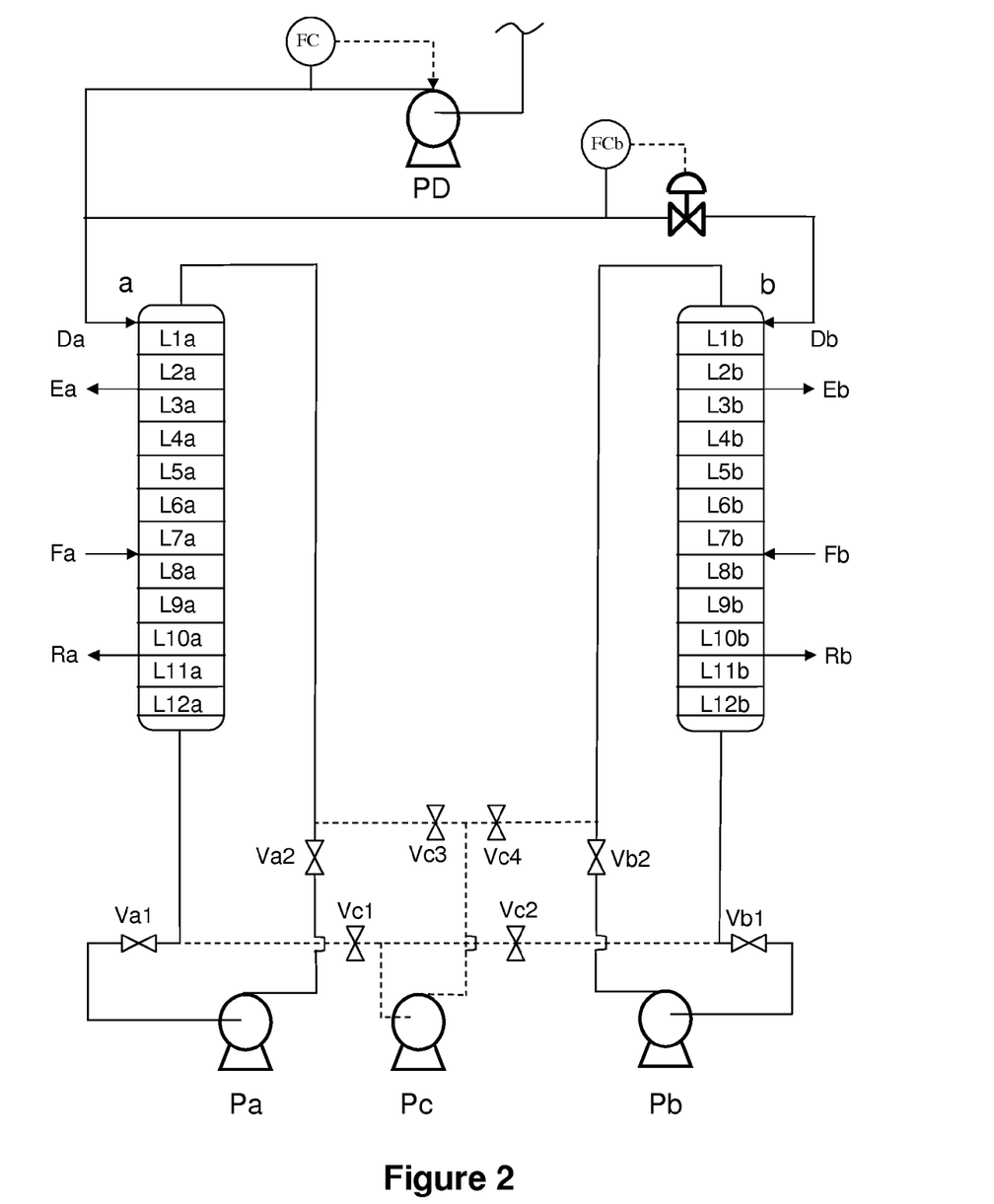
FIG. 2 represents the device of the invention, constituted by 2 adsorbers (a and b) each with 12 beds (L1$a$ to L12$a$ for adsorber a, and L1$b$ to L12$b$ for adsorber b).

The fact that two adsorption adsorbers are used in parallel in the process of the invention means that:
- a single pump replaces the feed supply pump(s) and a single pump replaces the desorbant supply pump(s);
- a single replacement recirculation pump (Pc) is available, this single replacement pump having a capacity to be used either to replace the recirculation pump (Pa) used on the first adsorber (a), or to replace the recirculation pump (Pb) employed on the second adsorber (b). When the pump Pc is used to replace the pump Pa, valves Va1 and Va2 are closed, and valves Vc1 and Vc3 are opened. When the pump Pc is used to replace the pump Pb, valves Vb1 and Vb2 are closed and valves Vc2 and Vc4 are open;
- only one automated control means is used for the two adsorbers;
- only a single in-line device is used to analyse the concentrations in the adsorbers. Such devices are described in particular in patent FR 2 942 879;
- all of the information necessary for control and operation of the process are centralized in a single control room.

In a further aspect, the invention concerns a method for transforming a process for the production of high purity para-xylene in a 24-bed simulated moving bed containing two 12-bed adsorbers in series into a process in accordance with the present invention, i.e. comprising two adsorbers each with twelve beds connected in parallel.

This method consists of modifying (also known as remodelling) an existing facility in order to improve its productivity.
- the twelfth bed of the first adsorber (a) is connected to the first bed of said first adsorber via a line containing at least one recirculation pump (Pa);
- the twelfth bed of the second adsorber (b) is connected to the first bed of said second adsorber via a line containing at least one recirculation pump (Pb).

The system for controlling and regulating the feed and desorbant injection and the extract and raffinate withdrawal flow rates for the 24-bed adsorption step is adapted so as to be able to independently manage the injection and withdrawal flow rates in each of the two adsorbers of the remodelled process of the invention.

For the injection devices, this operation could be carried out:
- either by doubling up the pump+measurement means system in order to regulate the flow injected into each of the adsorbers;
- or, with the aim of minimizing costs, by using the pre-existing pump and the measurement means which will manage the two streams to be injected together and by adding a system for measuring and regulating the flow supplying one of the two adsorbers.

When the supply or withdrawal of fluids over all of the plates of the existing 24 bed process is provided by a plurality of programmed on-off valves, no supplemental modifications have to be made to the supply and withdrawal networks. When the supply or withdrawal of fluids over all of the plates of the existing 24-bed process is provided by using a rotary multi-way valve, these functions will preferably be provided by using two rotary multi-way valves (by optionally recycling the pre-existing valve to one of the two ports after adaptation).

Figure 1:
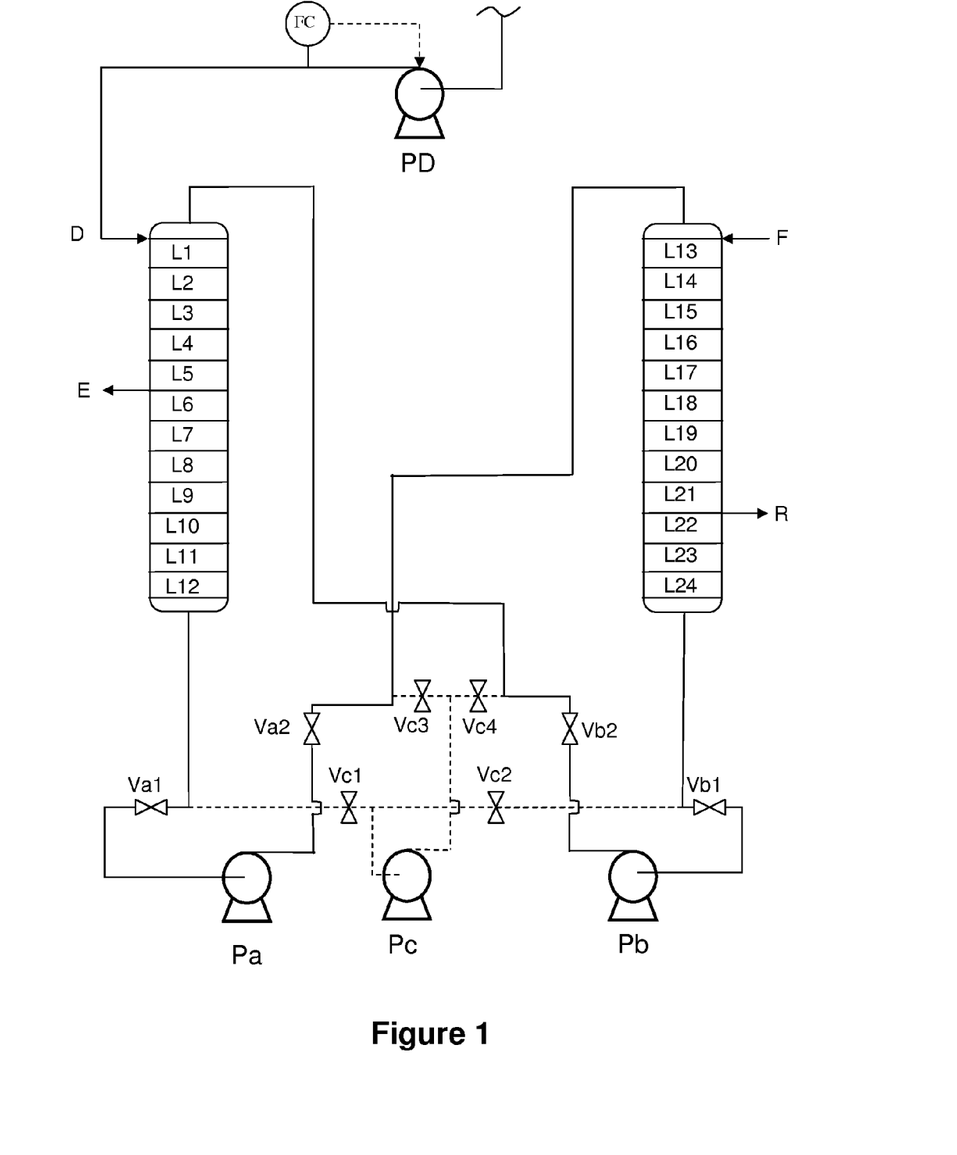
FIG. 1 represents the prior art process and thus comprises two 12-bed adsorbers each associated in series, which is equivalent to one 24 bed unit.

In the case of an existing 24 bed unit constituted two times twelve beds in series, the principal stream moves from the bottom of the first adsorber towards the head of the second adsorber and from the bottom of the second adsorber towards the head of the first adsorber, as can be seen in FIG. 1.

The streams from the bottoms of the two adsorbers are then reorientated to move towards the head of the adsorber from which they issue by modifying the valves and lines as shown in FIG. 2. The bottom stream from the adsorber a) is recycled to the head of said adsorber a) and the bottom stream from the adsorption b) is recycled to the head of said adsorber b).

The configuration (mean number of beds per zone) of the two adsorbers may be in accordance with one of the 3 variations discussed above, i.e.:
- with a fixed number of beds in each of the chromatographic zones for both adsorbers;
- with a variable number of beds for one adsorber and fixed for the other;
- with a variable number of beds for both adsorbers.

EXAMPLES

The invention will be better understood from the three examples below.

Example 1

In Accordance with the Prior Art

Consider a SCC unit constituted by 24 beds with a length of 1.1 m and an internal radius of 1.05 m, with a feed injection, a desorbant injection, an extract withdrawal and a raffinate withdrawal.

The adsorbent employed is a zeolitic BaX type solid and the desorbant is para-diethylbenzene. The temperature is 175° C. and the pressure is 15 bars. The quantity of water is 95 ppm (by weight).

The feed is composed of 21.6% para-xylene, 20.8% ortho-xylene, 47.9% meta-xylene and 9.7% ethylbenzene.

The SCC unit is constituted by 24 beds separated by distributor plates. An injection network and a withdrawal network are associated with each distributor plate. The rinsing device used is the modulated bypass fluid flow rate device as described in patent WO 2010/020715. The synchronicity is 100% in each zone.

The shifts for the various injection and withdrawal points are simultaneous. The beds are distributed in the 4 chromatographic zones in accordance with the configuration: 5/9/7/3
i.e. the distribution of the beds is as follows:
- 5 beds in zone 1 (between the desorbant D injection and the extract E withdrawal);
- 9 beds in zone 2 (between the extract E withdrawal and the feed F injection);
- 7 beds in zone 3 (between the feed F injection and the raffinate R withdrawal);
- 3 beds in zone 4 (between the raffinate withdrawal R and the desorbant D injection).

The feed and desorbant injection flow rates (defined by assuming a reference temperature of 40° C.) are as follows:
0.6102 m³/min for the feed;
0.7715 m³/min for the desorbant.

In addition, the flow rate for zone 4 is 1.8807 m³/min and the extract withdrawal flow rate is 0.3966 m³/min The switch period employed is 71.0 seconds.

By simulation, a para-xylene purity of 99.88% is obtained with a yield of para-xylene of 98.67%, and with a productivity of 72.5 $kg_{PX} \cdot h^{-1} \cdot m^{-3}$.

Example 2

In Accordance with the Invention

Consider a unit in accordance with the invention constituted by two adsorbers each with 12 beds. Each bed has a length of 1.1 m and an internal radius of 1.05 m.

The adsorbent employed is a zeolitic BaX type solid and the desorbant is para-diethylbenzene. The temperature is 175° C. and the pressure is 15 bars. The water content is 110 ppm (by weight).

The feed is composed of 21.6% para-xylene, 20.8% ortho-xylene, 47.9% meta-xylene and 9.7% ethylbenzene.

Each adsorber is constituted by 12 beds separated by distributor plates. An injection network and a withdrawal network are associated with each distributor plate. The rinsing device used is the modulated bypass fluid flow rate device as described in patent WO 2010/020715. The synchronicity is 100% in each zone.

For each of the adsorbers, the shifts for the various injection and withdrawal points are simultaneous. In each of the adsorbers, the beds are distributed in the 4 chromatographic zones in accordance with the configuration:
 2/5/3/2
i.e. the distribution of the beds is as follows:
 2 beds in zone 1 (between the desorbant D injection and the extract E withdrawal);
 5 beds in zone 2 (between the extract E withdrawal and the feed F injection);
 3 beds in zone 3 (between the feed F injection and the raffinate R withdrawal);
 2 beds in zone 4 (between the raffinate withdrawal R and the desorbant D injection).

For each of the two adsorbers, the feed and desorbant injection flow rates (defined by assuming a reference temperature of 40° C.) are as follows:
 0.4126 m³/min for the feed;
 0.5583 m³/min for the desorbant.

In addition, for each of the adsorbers, the flow rate for zone 4 is 1.2566 m³/min and the extract withdrawal flow rate is 0.3201 m³/min The switch period employed is 102.4 seconds.

By simulation, a para-xylene purity of 99.72% is obtained with a yield of para-xylene of 98.08%, and with a productivity of 97.5 $kg_{PX} \cdot h^{-1} \cdot m^{-3}$ considering the unit as a whole constituted by the two adsorbers.

Example 3

In Accordance with the Invention

Consider a unit in accordance with the invention constituted by two adsorbers each with 12 beds. Each bed had a length of 1.1 m and an internal radius of 1.05 m.

In each adsorber, the adsorbent employed is a zeolitic BaX type solid and the desorbant is para-diethylbenzene. The temperature is 175° C. and the pressure is 15 bars. The water content is 110 ppm (by weight).

The feed is composed of 21.6% para-xylene, 20.8% ortho-xylene, 47.9% meta-xylene and 9.7% ethylbenzene.

Each adsorber is constituted by 12 beds separated by distributor plates. An injection network and a withdrawal network are associated with each distributor plate. The rinsing device used is the modulated bypass fluid flow rate device as described in patent WO 2010/020715. The synchronicity is 100% in each zone.

For each of the adsorbers, the shifts for the various injection and withdrawal points are not simultaneous, in order to obtain non-integral chromatographic zone lengths (as disclosed in patent U.S. Pat. No. 6,136,198). In each of the two adsorbers, the beds are distributed in the 4 chromatographic zones in accordance with the configuration:
 2.2/4.8/3.2/1.8
i.e. the distribution of the beds is as follows during one period (by convention, the start and end of a period is defined by the shift of the desorbant injection points):
 from the start of the period to 81.92 seconds (defined with respect to the start of the period), there are:
  2 beds in zone 1 (between the desorbant D injection and the extract E withdrawal);
  5 beds in zone 2 (between the extract E withdrawal and the feed F injection);
  3 beds in zone 3 (between the feed F injection and the raffinate R withdrawal);
  2 beds in zone 4 (between the raffinate withdrawal R and the desorbant D injection).
 from 81.92 seconds (defined with respect to the start of the period) to the end of the period, there are:
  3 beds in zone 1 (between the desorbant D injection and the extract E withdrawal);
  4 beds in zone 2 (between the extract E withdrawal and the feed F injection);
  4 beds in zone 3 (between the feed F injection and the raffinate R withdrawal);
  1 bed in zone 4 (between the raffinate withdrawal R and the desorbant D injection).

For each of the two adsorbers, the feed and desorbant injection flow rates (defined by assuming a reference temperature of 40° C.) are as follows:
 0.4126 m³/min for the feed;
 0.5460 m³/min for the desorbant.

In addition, for each of the adsorbers, the flow rate for zone 4 is 1.2433 m³/min and the extract withdrawal flow rate is 0.2949 m³/min The switch period employed is 102.4 seconds.

By simulation, a para-xylene purity of 99.70% is obtained with a yield of para-xylene of 98.20%, and with a productivity of 97.6 $kg_{PX} \cdot h^{-1} \cdot m^{-3}$ considering the unit as a whole constituted by the two adsorbers.

Example 4

In Accordance with the Invention

Consider a unit in accordance with the invention constituted by two adsorbers each with 12 beds. Each bed had a length of 1.1 m and an internal radius of 1.05 m.

In each adsorber, the adsorbent employed is a zeolitic BaX type solid and the desorbant is para-diethylbenzene. The temperature is 175° C. and the pressure is 15 bars. The water content is 110 ppm (by weight).

The feed is composed of 21.6% para-xylene, 20.8% ortho-xylene, 47.9% meta-xylene and 9.7% ethylbenzene.

Each adsorber is constituted by 12 beds separated by distributor plates. An injection network and a withdrawal network are associated with each distributor plate. The rinsing device used is the modulated bypass fluid flow rate device as described in patent WO 2010/020715. The synchronicity is 100% in each zone.

In the first adsorber, the shifts for the various injection and withdrawal points are simultaneous, and the beds are distributed in the 4 chromatographic zones in accordance with the configuration:

2/5/3/2 i.e. the distribution of the beds is as follows:
- 2 beds in zone 1 (between the desorbant D injection and the extract E withdrawal);
- 5 beds in zone 2 (between the extract E withdrawal and the feed F injection);
- 3 beds in zone 3 (between the feed F injection and the raffinate R withdrawal);
- 2 beds in zone 4 (between the raffinate withdrawal R and the desorbant D injection).

In the first adsorber, the feed and desorbant injection flow rates (defined by assuming a reference temperature of 40° C.) are as follows:
- 0.4126 m$^3$/min for the feed;
- 0.5583 m$^3$/min for the desorbant.

In addition, in the first adsorber, the flow rate for zone 4 is 1.2566 m$^3$/min and the extract withdrawal flow rate is 0.3201 m$^3$/min The switch period employed is 102.4 seconds.

In the second adsorber, the shifts for the various injection and withdrawal points are not simultaneous, in order to obtain non-integral chromatographic zone lengths (as disclosed in patent U.S. Pat. No. 6,136,198). The beds are distributed in the 4 chromatographic zones in accordance with the configuration:

2.2/4.8/3.2/1.8 i.e. the distribution of the beds is as follows during one period (by convention, the start and end of a period is defined by the shift of the desorbant injection points):

from the start of the period to 81.92 seconds (defined with respect to the start of the period), there are:
- 2 beds in zone 1 (between the desorbant D injection and the extract E withdrawal);
- 5 beds in zone 2 (between the extract E withdrawal and the feed F injection);
- 3 beds in zone 3 (between the feed F injection and the raffinate R withdrawal);
- 2 beds in zone 4 (between the raffinate withdrawal R and the desorbant D injection).

from 81.92 seconds (defined with respect to the start of the period) to the end of the period, there are:
- 3 beds in zone 1 (between the desorbant D injection and the extract E withdrawal);
- 4 beds in zone 2 (between the extract E withdrawal and the feed F injection);
- 4 beds in zone 3 (between the feed F injection and the raffinate R withdrawal);
- 1 bed in zone 4 (between the raffinate withdrawal R and the desorbant D injection).

In the second adsorber, the feed and desorbant injection flow rates (defined by assuming a reference temperature of 40° C.) are as follows:
- 0.4126 m$^3$/min for the feed;
- 0.5460 m$^3$/min for the desorbant.

In addition, in the second adsorber, the flow rate for zone 4 is 1.2433 m$^3$/min and the extract withdrawal flow rate is 0.2949 m$^3$/min The switch period employed is 102.4 seconds.

By simulation, a para-xylene purity of 99.71% is obtained with a yield of para-xylene of 98.14%, and with a productivity of 97.6 kg$_{PX}$.h$^{-1}$.m$^{-3}$ considering the unit as a whole constituted by the two adsorbers.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 11/01.855, filed Jun. 16, 2011, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for simulated counter-current separation of xylenes comprising a first adsorption step using two adsorbers each containing twelve beds, each of the adsorbers having a line for introducing feed (F), a line for introducing eluent (D), a line for withdrawing extract (E) and a line for withdrawing raffinate (R) and being divided into 4 chromatographic zones defined as follows:
  zone 1: para-xylene desorption zone, included between the injection of desorbant D and the removal of extract E;
  zone 2: isomers of para-xylene desorption zone, included between the removal of the extract E and the injection of the feed to be fractionated F;
  zone 3: para-xylene adsorption zone, included between the injection of the feed and the withdrawal of the raffinate R;
  zone 4: zone located between the withdrawal of the raffinate R and the injection of the desorbant;
and the two adsorbers functioning in parallel, i.e. the twelfth bed of the first adsorber (a) is connected to the first bed of said adsorber via a line containing a recirculation pump, and the twelfth bed of the second adsorber is connected to the first bed of said second adsorber via a line containing a recirculation pump which is distinct from the preceding pump;
the process further comprising:
  a step for distilling a mixture of the two raffinates in a single distillation column from which a mixture of xylenes depleted in para-xylene is withdrawn overhead and the desorbant, which is recycled, is withdrawn from the bottom;
  a step for distilling the two extracts in one or two distillation column(s) from which substantially pure para-xylene with a purity of more than 99.7% by weight is withdrawn overhead and the desorbant is withdrawn from the bottom and recycled.

2. A process for simulated counter-current separation of xylenes according to claim 1, in which the 12 beds of each adsorber are distributed in the 4 chromatographic zones in the following manner:
  2 beds in zone 1;
  5 beds in zone 2;
  3 beds in zone 3;
  2 beds in zone 4.

3. A process for simulated counter-current separation of xylenes according to claim 1 in which, for one of the adsorbers, the shifts of the 2 injection points and the 2 withdrawal points are simultaneous, the 12 beds of the adsorber being distributed in the 4 chromatographic zones in the following manner:
   2 beds in zone 1;
   5 beds in zone 2;
   3 beds in zone 3;
   2 beds in zone 4;
   and for the other adsorber, the shifts of the 2 injection points and the 2 withdrawal points are not simultaneous, in order to obtain mean numbers of beds per zone which are not whole numbers during a cycle, the numbers of beds per zone for this adsorber being as follows:
   2.5 (+ or −0.5) beds in zone 1;
   4.5 (+ or −0.5) beds in zone 2;
   3.5 (+ or −0.5) beds in zone 3;
   1.5 (+ or −0.5) beds in zone 4.

4. A process for simulated counter-current separation of xylenes according to claim 1 in which, for each of the adsorbers, the shifts of the 2 injection points and the 2 withdrawal points are not simultaneous, in order to obtain mean numbers of beds per zone which are not whole numbers during a cycle, the numbers of beds per zone for each of the adsorbers being as follows:
   2.5 (+ or −0.5) beds in zone 1;
   4.5 (+ or −0.5) beds in zone 2;
   3.5 (+ or −0.5) beds in zone 3;
   1.5 (+ or −0.5) beds in zone 4.

5. A process for simulated counter-current separation of xylenes according to claim 1, in which the two adsorbers each contain twelve beds separated by plates Pi with a chamber for distribution and/or extraction of fluids and programmed means for sequential distribution and extraction of said fluids, said programmed means for distribution and extraction of fluids being constituted, for each plate Pi, by at least 4 programmed 2-way on-off valves to respectively manage the 2 fluid supplies for feed (F) and eluent (D) and the 2 withdrawals, for extract (E) and raffinate (R).

6. A process for simulated counter-current separation of xylenes according to claim 1, in which each adsorber uses a rotary multi-way valve which can manage the supply of the feed (F), the supply of the eluent (D), the withdrawal of the extract (E) and the withdrawal of the raffinate (R) for all of the plates.

7. A process for simulated counter-current separation of xylenes according to claim 1, in which the adsorbent solid is an agglomerated zeolitic adsorbent solid comprising small crystals (i.e. with a diameter of 2 μm or less) of X zeolite at least 90% exchanged either by barium ions alone or by barium ions and potassium ions, the exchangeable sites occupied by potassium representing up to ⅓ of the exchangeable sites occupied by barium+potassium ions, and a proportion of inert binder of less than 15% by weight.

8. A process for simulated counter-current separation of xylenes according to claim 1, in which the desorbant is para-diethylbenzene.

9. A process for simulated counter-current separation of xylenes according to claim 1, in which:
   a) the adsorption temperature is in the range 100° C. to 250° C., preferably in the range 120° C. to 180° C.;
   b) the adsorption pressure is in the range between the bubble-point pressure of xylenes at the temperature of the process and $30 \times 10^5$ Pa;
   c) the ratio of the flow rates of desorbant to feed is in the range 0.7 to 2.5;
   d) the recycle ratio of the eluent is in the range 2.5 to 12, preferably in the range 3.5 to 6;
   e) the duration of the cycle followed by the adsorbers is in the range 14 to 30 minutes, preferably in the range 18 to 23 minutes;
   f) the mean linear velocity with respect to the empty reactor is in the range 0.7 cm/s to 1.4 cm/s, preferably in the range 0.85 cm/s to 1.1 cm/s;
   g) the water content in the liquid phase is maintained at a content in the range 70 to 140 ppm (by weight), preferably in the range 80 to 120 ppm (by weight).

10. A process for simulated counter-current separation of xylenes according to claim 1, in which the unit constituted by two adsorbers in parallel further comprises:
   a single pump replacing the pump(s) for supplying feed (F) and a single pump replacing the pump(s) supplying desorbant (D);
   a single replacement recirculation pump, said single replacement pump being able to be used either to replace the recirculation pump employed on the first adsorber, or to replace the recirculation pump employed on the second adsorber.

11. A method for adapting a process for the production of para-xylene in a 24-bed simulated moving bed composed of two 12-bed adsorbers in series into a process according to claim 1, the method being characterized in that it comprises the steps of:
   a) connecting the twelfth bed of the first adsorber (a) to the first bed of said first adsorber via a line containing at least one recirculation pump (Pa);
   b) connecting the twelfth bed of the second adsorber (b) to the first bed of said second adsorber via a line containing at least one recirculation pump (Pb);
   c) adapting the system for measuring and regulating the feed and desorbant injection flow rates and the extract and raffinate withdrawal flow rates in order to be able to independently manage the injection and withdrawal flow rates in each of the two adsorbers;
   d) modifying the automated control means of the process in order to be able to control and monitor the two adsorbers in parallel.

* * * * *